United States Patent [19]

Scher

[11] Patent Number: 4,643,764

[45] Date of Patent: Feb. 17, 1987

[54] MULTIPLE TYPES OF MICROCAPSULES AND THEIR PRODUCTION

[75] Inventor: Herbert B. Scher, Moraga, Calif.

[73] Assignee: Stauffer Chemical Company, Westport, Conn.

[21] Appl. No.: 696,972

[22] Filed: Jan. 31, 1985

Related U.S. Application Data

[63] Continuation-in-part of Ser. No. 569,066, Jan. 9, 1984, abandoned.

[51] Int. Cl.$^4$ ............... A01N 43/00; A01N 25/28; B01J 13/02
[52] U.S. Cl. .................... 71/100; 71/88; 71/DIG. 1; 264/4.7; 424/19; 424/32; 424/84; 424/DIG. 8; 428/402.21; 514/104; 514/963
[58] Field of Search .......... 264/4.7; 428/402.21; 424/32, DIG. 8, 84; 71/88, 100, DIG. 1; 514/104, 464

[56] References Cited

U.S. PATENT DOCUMENTS

| | | | |
|---|---|---|---|
| 3,041,289 | 6/1962 | Katchen et al. | 428/402.2 X |
| 3,490,454 | 1/1970 | Goldfarb et al. | 424/25 X |
| 4,285,720 | 8/1981 | Scher | 264/4.7 X |

*Primary Examiner*—Richard D. Lovering

*Attorney, Agent, or Firm*—Paul R. Martin

[57] ABSTRACT

In a process of encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps
(a) providing at room temperature a dispersion of
  (i) a water-immiscible phase comprising the water-immiscible material to be encapsulated and organic polyisocyanates in
  (ii) an aqueous phase comprising a solution of water, a surfactant and a protective colloid; and
(b) heating and maintaining said dispersion in a temperature range of about 40° C. to about 90° C., whereupon said water-immiscible material is encapsulated within discrete polyurea capsular enclosures directly usable without further separation or purification, the improvement comprising providing a plurality of water-immiscible phases each comprising at least one individually distinct wall-forming organic polyisocyanate monomer, and a water-immiscible material to be encapsulated in a polyurea wall formed from said polyisocyanate monomer, and sequentially or simultaneously dispersing each of said water-immiscible phases in said aqueous phase.

12 Claims, No Drawings

MULTIPLE TYPES OF MICROCAPSULES AND THEIR PRODUCTION

CROSS REFERENCE TO RELATED APPLICATIONS

This is a continuation-in-part of application Ser. No. 569,066, filed Jan. 9, 1984, and now abandoned.

BACKGROUND OF THE INVENTION

The present invention relates to a process for producing microcapsules of varying size and wall thicknesses, substantially simultaneously in one reactor vessel.

Microcapsule technology has been in existence for a number of years, and is particularly adaptable to herbicide technology wherein specific active herbicidal agents are incorporated into microcapsules having protective wall coatings for later dissemination in a variety of uses.

A basic patent dealing with microcapsule technology is U.S. Pat. No. 4,285,720, which disclosures are incorporated by reference herein.

As stated in that patent, microcapsules have a variety of uses, such as for containing dyes, inks, chemical reagents, pharmaceuticals, flavoring materials, fungicides, bactericides, pesticides, herbicides, insecticides and the like. These materials can be dissolved, suspended or otherwise dispersed in or as the material to be enclosed by the capsule.

In that patent, the basic procedure for microencapsulation is described, involving the reaction between polyisocyanate monomers, to produce the microcapsule skin.

DESCRIPTION OF THE PRIOR ART

In the prior art, as described in U.S. Pat. No. 4,285,720, the process for the production of microcapsules has dealt with the production of microcapsules which are unimodal in terms of wall thicknesses, and size. If microcapsules of differing modalities were desired, an entirely separate reaction would have to be conducted. Microcapsules of differing dimensions and wall thicknesses would be desirable, for example, to provide a soil insecticide formulation with high initial activity and good residual activity. To achieve these goals in the formulation would require two different sized capsules with differing wall thicknesses. This could be done by using separate reaction vessels for each modality, however, this is an inefficient method of manufacture. Accordingly, it would be desirable to develop a more efficient process for the production of microcapsules of multiple dimensions, whether in terms of size or wall thickness, in which the microcapsules can be produced substantially simultaneously in the same reaction vessel.

This invention is thus concerned with such a method.

SUMMARY OF THE INVENTION

In U.S. Pat. No. 4,285,720 there is described a process of encapsulating water-immiscible material within discrete capsules of polyurea without addition of a second reactant, whereby hydrolysis of an isocyanate monomer to form an amine takes place, which in turn reacts with another isocyanate monomer to form polyurea, which comprises the steps of (a) providing at room temperature, a dispersion of
(i) a water-immiscible phase comprising the water-immiscible material to be encapsulated and an organic polyisocyanate in
(ii) an aqueous phase comprising a solution of water, a surfactant and a protective colloid; and
(b) heating and maintaining the dispersion in a temperature range of about 40° C. to about 90° C., whereupon the water-immiscible material is encapsulated within discrete polyurea capsular enclosures directly usable without further separation or purification.

The present invention is an improvement upon that process in which the dispersion of (i) is a plurality of water-immiscible phases comprising in each phase a water-immiscible material to be encapsulated and an organic polyisocyanates, and wherein each of the organic phases vary from each other in some respect with regard to percentages of ingredients such that each of the plurality of phases provides a separate and distinct modality and the finished product when each of the plurality of phases is either simultaneously or sequentially admixed in the same reaction vessel.

In all other respects the process is the same as that described in U.S. Pat. No. 4,285,720, with all of the limitations therein with respect to process conditions.

In all cases, within the practice of the present invention, the effective procedure involves first, producing, as by simple agitation, a solution of water, a suitable surfactant and protective colloid. These three ingredients comprise the aqueous phase or continuous phase of the process. The aqueous or continuous phase is essentially free of any components that will react with the material therein or any of such group of materials. The surfactant and protective colloid in the aqueous phase do not enter into the polycondensation reaction by which the capsule wall is formed.

By way of further exemplification, the surfactants in the aqueous or continuous phase can be described as nonionic, anionic or cationic surfactants in the HLB (hydrophile-lipophile balance) range from about 12 to about 16. There are many surfactants which satisfy this HLB range requirement. Among the acceptable surfactants are the compounds known as sodium isopropyl naphthalene sulfonate, polyoxyethylenesorbitol oleate laurate, ethoxylated nonylphenols, however, the preferred surfactant is of the class polyethylene glycol ethers of linear alcohols. Whereas the surfactant is described herein as placed in the aqueous phase, it can also be placed in the organic phase or phases. Without specific reference to the phase in which the surfactant is placed, there will be a partitioning and distribution of the surfactant between each phase upon the mixing of the phases depending upon the relative solubility therein. Use of a surfactant may be omitted provided that a sufficiently high shear rate is employed to form the dispersion. In the preferred embodiment of this invention a surfactant is employed. The range of surfactant concentration found most acceptable in this system is from about 0.01% to about 3.0% by weight based on the aqueous phase. Higher concentrations of surfactant may be used without increased ease of dispersibility.

Also present in the aqueous or continuous phase is a protective colloid which can be selected from a wide range of such materials. The usable protective colloids can be exemplified by the following: polyacrylates, methyl cellulose, polyvinyl alcohol, polyacrylamide poly(methylvinyl ether/maleic anhydride) and polymeric lignin sulfonates. The amount of colloid employed will depend upon various factors such as molecular weight, type and effectiveness within the media, compatability and the like. It has been found that the protective colloid can be added to the aqueous phase prior to addition of the organic phases or following the dispersion thereof. As another alternative, the protective colloid can be added partially prior to addition of the organic phases and partially after the dispersion step. Generally, from about 0.1% to about 5% by weight based on the aqueous phase is used.

Each of the other phases, known as the organic phases, comprises the material to be encapsulated, and at least one polyisocyanate, each polyisocyanate being an individually wall-forming monomer. The material to be encapsulated can be used in a concentrated form or in a solution of a water-immiscible solvent.

Each polyisocyanate is an individual wall-forming monomer, thus if two or more distinct polyisocyanates are used, capsules of differing wall thicknesses and wall compositions can be produced. The material to be encapsulated can be used as the solvent for the polyisocyanate(s). However, to achieve a desired concentration of active material in the final product, a waterimmiscible organic solvent can be used to dissolve the material to be encapsulated and polyisocyanate(s). The organic phases containing the material to be encapsulated and the polyisocyanate(s) are added simultaneously to the aqueous phase. Separate phases may also be added sequentially, if desired. Preferably, the phases are added sequentially but close together, one after the other. Each phase of the material to be encapsulated and the polyisocyanate(s) are pre-mixed to obtain a homogeneous phase before addition to and mixing with the aqueous phase. The total amount of the organic phases may vary from about 1% to about 75% by volume of the aqueous phase present in the reaction vessel. The concentrations in the lower end of the range are relatively undesirable since they result in a very dilute suspension of capsules. The preferred total amount of organic phase is about 25% to about 50% by volume.

The nature of the organic polyisocyanate(s) determines the release properties of the capsules formed by this process. The polyisocyanates also determine the structural physical strength of the capsular skin. The organic polyisocyanates contemplated in this process include those members of the aromatic polyisocyanate class which includes the aromatic diisocyanates, the aliphatic diisocyanate class, high molecular weight linear aliphatic diisocyanates and the isocyanate prepolymers. Representative of the aromatic diisocyanates and other polyisocyanates are the following: 1-chloro-2,4-phenylene diisocyanate, m-phenylene diisocyanate, p-phenylene diisocyanate, 4,4'-methylenebis(phenyl isocyanate), 2,4-tolylene diisocyanate, tolylene diisocyanate (60% 2,4-isomer, 40% 2,6-isomer) 2,6-tolylene diisocyanate, 3,3'-dimethyl-4,4'-diphenylene diisocyanate, 4,4'-methylenebis(2-methylphenyl isocyanate), 3,3'-di-methoxy-4,4'-biphenylene diisocyanate, 2,2',5,5'-tetramethyl-4,4'-bi-phenylene diisocyanate, 80% 2,4- and 20% 2,6-isomer of tolylene diisocyanate and polymethylene polyphenylisocyanate (PAPI). It is highly desirable to use combinations of the above-mentioned organic polyisocyanates. Such combinations as, for example, polymethylene polyphenylisocyanate and tolylene diisocyanate, containing 80% 2,4- and 20% 2,6-isomers, produce excellent capsular enclosures with exceptional controlled release properties.

The amount of organic polyisocyanate used in the process will determine the wall content of the capsules formed therein. Generally, based on each of the organic phases, there will be greater than about 2% by weight organic polyisocyanate present. However, this is by no means limiting and a greater amount can be used that is approaching 100%. Clearly, 100% would not be entirely desirable since this would result in a product with no encapsulated material. The preferred range is from about 2% to about 75% by weight of organic polyisocyanate(s), thereby forming an encapsulated product having a corresponding wall content, i.e., about 2% to about 75%. More particularly, the preferred range is from about 5% to about 50% wall content.

In accordance wth preferred practice of the present invention, the following general steps comprise the process which utilizes the substantially immiscible phases described above. In essence, the process comprises establishing a physical dispersion of each of the organic phases in the aqueous or continuous phase, such dispersion thereby establishing droplets of desired size in the aqueous phase. Thereafter, by adjusting the pH of the resulting mixture, and temperature within the appropriate temperature range, the desired condensation reaction is thereby effected at the interfaces between the droplets and the continuous phase. Certain variations in the sequence of steps between adjustment of the pH and addition of required heat will be apparent in the following discussion and examples.

The temperature of the multiple-phase mixture, that is, the dispersion of the organic phases in the aqueous phase, is raised to about 40° C. to about 60° C. The temperature range for the condensation reaction within the present invention is between about 20° C. to about 90° C. Whereas the heat to initiate the reaction can be applied to the dispersion of the organic phase in the aqueous phase simultaneously or after the adjustment of the pH to the desired value, the aqueous phase can be heated to the required temperature prior to the steps of addition of the organic phases and dispersion. In this alternative procedure, the adjustment of the pH is performed after the dispersion is accomplished and the pH is maintained within the limits to be discussed below.

Within one embodiment of the present invention, it has been found that a catalyst capable of increasing the rate of isocyanate hydrolysis, for example, the basic amine type, may be added to each of the organic phases or aqueous phase prior to the initiation of the desired condensation reaction. However, this step is not necessary to the successful practice of the present invention. Increased temperature and catalyst can be used simultaneously to effect the desired polycondensation reaction. The catalyst in such a procedure is added preferably to the organic phases and is added to the system at the time of mixing of the aqueous and each of the organic phases. Various catalysts have been found acceptable, their selection will depend upon factors easily determinable by one skilled in the art. It has been found that certain basic organic amines, preferably the tertiary amines, and alkyl tin acetates such as tributyl tin acetate and di-n-butyl tin diacetate are acceptable catalysts. When an alkyl tin acetate is used, about 0.001% to about 1% by weight based on the organic phase is employed. Included among the basic total organic tertiary amines are triethylene diamine, N,N,N',N'-tetramethyl-1,3-butane-diamine, triethylamine, tri-nbutylamine and the like. The amount of catalyst will vary with the particular system and conditions. When a basic organic amine is used, about 0.01% to about 10% by weight based on the total of the organic phases is employed.

Oftentimes it will be found that water will be slightly soluble in the water-immiscible material to be encapsulated. The amount of water which will be dissolved in the material to be encapsulated will depend upon the nature of the material. Usually the amount of water dissolved will be relatively minor. However, when using a water-immiscible material that can dissolve an appreciable quantity of water, slight deviation in the normal processes described herein is preferred. In such a system it has been found that particles with poorly defined wall structure result. Well-defined microcapsules within the description of this invention can be prepared by adding an appropriate catalyst to the aqueous phase after the emulsion is formed. Thereby, the bulk of the polymerization takes place at the interface where the catalyst is present. No heating of the process mixture is advised, otherwise polymer will form not only on the surface, but an increased proportion will form within the water-immiscible material that can dissolve an appreciable amount of water. This procedure is preferably performed at about room temperature (15° to 30° C.). This method of addition of the catalyst to the aqueous phase after dispersion is not limited to encapsulation of only water-immiscible material that can dissolve appreciable quantity of water, but finds general applicability with any water-immiscible material herein discussed and described.

It is satisfactory to prepare the aqueous phase as described above. While stirring the aqueous phase, the organic phases are added, preferably in a pre-mixed state. As previously stated, these organic phases can be added simultaneously or sequentially. Upon addition of the organic phases to the aqueous phase, a suitable dispersing means to disperse one liquid into the other is employed. Any high shear device can be used conveniently to obtain the desired droplet size within the range of from about 0.5 microns to about 4,000 microns. The actual range will depend upon the desired end use. As an example, the preferred range for most pesticidal applications is from about 1 micron to about 100 microns. The instant process is applicable to preparing widely varied but uniform sized capsules. Once the proper droplet size is obtained, the dispersion means employed to establish the desired droplet size is discontinued. Only mild agitation is required for the balance of the process.

The process of the instant invention is capable of satisfactory performance and production of encapsulated material without adjustment to a specific pH value. That is, no adjustment of the pH of the system need be made during the encapsulation process. The encapsulation process will proceed at a pH value of between about 0 to about 14. The desirability of any adjustment of pH to a particular value will depend upon the nature of the systems' components, such as surfactant, colloid, catalyst, temperature, material to be encapsulated and the like. For example, if the pH is allowed to drop below about 7.0, carbon dioxide will be liberated during the course of the reaction. If it is desirable to eliminate this evolution of carbon dioxide, then adjustment can be made to a pH value of at least about 7.0. The pH can be adjusted after dispersion and maintained at that value for the remainder of the condensation reaction. The adjustment of the pH can take place in the aqueous phase prior to the addition and dispersion therein of the organic phases. The adjustment and maintenance of a particular pH throughout the reaction can be accomplished with various water soluble bases or acids nonreactive with the polyisocyanate intermediates. Preferably, concentrated sodium hydroxide (25% solution), potassium hydroxide, hydrochloric acid and the like can be used.

The evolution of carbon dioxide may cause considerable undesirable foam formation and/or volume expansion which interferes with the processing of the reaction mixture. An alternative to the adjustment of the pH in order to eliminate the excessive foam produced by the carbon dioxide evolution is the addition of a defoamer. By the use of a defoamer, it is possible to satisfactorily produce the encapsulated material at an acid pH without the addition of caustic to the acidic system. The defoamer can be added any any time to the processing mixture wherein said polymer capsular enclosures are formed to encapsulate a water-immiscible material.

Whereas the desired condensation reaction at the interface between the droplets and the continuous phase occurs very rapidly, the majority within the first one-half hour of reaction time, in order to insure near completion of the condensation reaction throughout the system, the reaction conditions are continued for from about 2 to 3 hours. Under properly adjusted conditions or with a proper catalyst, the reaction time can be shortened. At the end of this time, the formation of a capsule wall has been completed, thereby encapsulating the organic material within the skin of a polycondensate, and there exists a usable encapsulated product. A specific feature of the present invention, which is highly desirable, resides in the fact that for certain intended applications, no further separation or handling of the encapsulated material is required, i.e., the product is directly usable. The encapsulated material can be used for various direct applications at this point or indirectly by incorporating the material into other products.

The thickness or chemical compositions of the capsule walls can be selected or controlled in various ways. For example, these properties can be affected by control of the reaction condition, by chemical selection, especially in the reaction of cross-linkage which is determined by the functionality of the polyisocyanate in accordance with the invention. The thickness of the capsule skin can also be altered by varying the amounts of reactants within the individual organic phases. One convenient mode of controlling the size of the capsule is adjustment of the speed of agitation, that is, in bringing about the original dispersion of the organic phases, smaller capsules can be obtained with higher speeds of agitation resulting in a greater shearing force.

The capsules produced in accordance with the present invention can be utilized in the same manner as product of other encapsulation procedures. Thus, for example, encapsulated herbicides or insecticides can be embodied in dispersions for application purposes, for controlled release of the encapsulated material at the desired locality. Special utility is noted for the encapsulation of various volatile or unstable insecticides and herbicides. By encapsulation, premature volatilization or other deterioration of the material is avoided; such encapsulation can also serve the purpose of retarding or delaying action to the time when desired. Controlled release of these materials is important for environmental protection and the proper effect on the organism to be controlled, as well as decreased toxicity on beneficial organisms.

The present invention may be practiced in a batch or batch-like form or in a continuous or continuous-like form. When the invention is practiced in a manner resembling a batch process, all the various liquids and various reactants will be brought together and various steps determined by the proper time sequence into a single body of liquid. The batch process may be altered by using the suitable reactors such that a continuous or continuous-like form of the encapsulation process is achieved. In the continuous form of the inventive process, dispersion and agitation of the reacting phases may continuously be practiced at a proper rate to continuously form suitable dispersion of droplets in the continuous phase and such that a continuously supplied portion of the dispersion of droplets in a continuous phase is added to a reactor in which the pH can be adjusted and the appropriate heat applied to achieve the condensation. Within the continuous system, the proper rate for reaction may be obtained by selecting the appropriate conditions. Both the batch and continuous aspects of the present invention are highly desirable, and choice there between will rest solely with the desired manufacturing conditions.

This invention will be more readily understood by reference to the specific examples which follow which demonstrate the process described herein.

EXAMPLE I

Water (378 grams (g)) containing 2% Vinol 205, and 0.3% linear alcohol ethoxylate emulsifier (Tergitol 15-S-7) is placed into an open reactor vessel. In one separate container, 158.8 g methyl parathion technical, an insecticide, 9.7 g polymethylene polyphenol isocyanate (PAPI) and 3.2 g tolylene diisocyanate (TDI) are mixed together. In a second separate container 158.8 g methyl parathion technical, 9.7 g polymethylene polyphenyl isocyanate (PAPI) and 3.2 g tolylene diisocyanate (TDI), 5.2 g sudan green 4B dye (which imparts a deep blue color to the organic phase) are also mixed together. The first organic phase is then dispersed in the aqueous phase and emulsified with a high shear stirrer. The resulting particle size ranged from about 10 to 40 millimicrons. The second organic phase was then dispersed in the aqueous phase containing the first organic phase and the second organic phase was also emulsified (10–40μ) with a high shear stirrer. The temperature of the reactants was raised to about 60° C. over a 30 minute period of time. The temperature of the reaction mixture was maintained at 60° C. for approximately 2.5 hours in order to complete the interfacial polymerization.

Microscopic observation after heat-up showed the presence of colorless capsules and deep blue capsules in the 10–40 micron particle size range. There were no light blue capsules in this particle size range indicating that coalescence and redispersion of the two different particles had not occurred.

EXAMPLE II

A quantity of water (318 g) containing 2% Gantrez AN119, 0.22% Vinol 205, and 0.3% Tergitol 15-S-7 was placed in an open reactor vessel. In one separate container, 178.3 g Dyfonate technical, 21.0 g polymethylene polyphenyl isocyanate (PAPI) and 10.3 g tolylene diisocyanate (TDI) are mixed together. In a second separate container 178.3 g Dyfonate, 9.6 g PAPI and 4.8 g TDI were also mixed together. The first organic phase is then dispersed in the aqueous phase and emulsified with a high shear stirrer. The resulting particle size ranged from about 10 to 40 microns. The second organic phase was then dispersed in the aqueous phase containing the first organic phase and the second organic phase was also emulsified (10–40 microns) with a high shear stirrer. The temperature of the reactants was raised to about 60° C. over a 30 mixture period of time. The temperature of the reaction mixture was maintained at 60° C. for approximately 2.5 hours in order to complete the interfacial polymerization.

After the interfacial polymerization was completed, additional ingredients were added to the emulsion. These ingredients were 2.2 g Cellosize QP440, a suspending agent; 0.36 g Dowcide G, a biocide; and 11.6 g of a solution of 64% $FeCl_3.6H_2O$, which was a buffer. The Cellosize was added and dispersed over a 5 minute period, followed by the Dowcide G. The pH was then raised to approximately 9.0 and high speed shearing continued for approximately 20 minutes. Thereafter, the $FeCl_3$ solution was added slowly followed by 25 minutes of additional shearing at a pH of 11.0.

As previously mentioned and illustrated by the examples herein, the process for encapsulation of the instant invention provides capsules capable of controlling release of encapsulated organic material. Representative and especially of importance are the process and capsules comprising as a constituent in the organic phases herbicides of the class thiocarbamate such as S-ethyl diisobutylthiocarbamate, S-ethyl N,N-di-propylthiocarbamate, S-ethyl hexahydro-1H-azepine-1-carbothioate, S-propyl N,N-dipropylthiocarbamate, S-ethyl ethylcyclohexylthiocarbamate, S-propyl butylethylthiocarbamate; organophosphorus insecticides of the class organophosphono and phosphorothioates; and dithioates such as O-ethyl S-phenyl ethylphosphonodithioate, S-[(p-chlorophenylthio)methyl]O,O-di-methylphosphorodithioate, O,O-dimethyl O-p-nitrophenylphosphorothiaote, O,O-diethyl O-p-nitrophenylphosphorothiaote; and insect hormones and mimics such as:

Cecropia - Juvenile Hormone - I

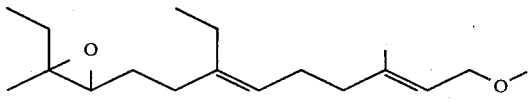

1-(4'-ethyl)-phenoxy-3,7-dimethyl-6,7-epoxy-trans-2-octene

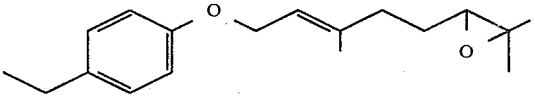

1-(3'-4'-methylenedioxy)phenoxy-3,7-dimethyl-6,7-epoxy-trans-2-nonene

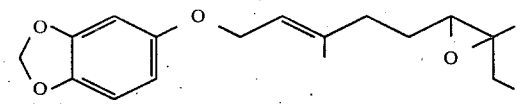

Ethyl 3,7,11-trimethyldodeca-2,4-dienoate

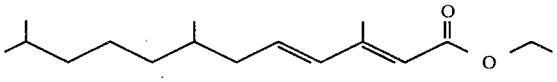

Isopropyl 11-methoxy-3,7,11-trimethyldodeca-2,4-dienoate

Capsules of compounds useful for plant disease control provide a route to long term control of disease using compounds generally regarded to have only short term effectiveness. Similarly, herbicides, nematocides, insecticides, rodenticides and soil nutrients can be encapsulated with useful results. Chemicals used for seed treatment are also readily encapsulated by the process of the invention. Other biological products can be encapsulated including: anthelmintics, lamphrey and slime control agents, algicides, swimming pool chemicals, miticides, acaracides, animal attractants, antiseptics, deodorants, disinfectants, mildewicides, and the like.

The material to be encapsulated utilizing the process of the instant invention can be of any type which is water-immiscible. The material need not consist of only one type, but may be a combination of two or more various types of water-immiscible materials. For example, employing an appropriate water-immiscible material, such a combination is an active herbicide and an active insecticide. Also contemplated is a water-immiscible material to be encapsulated which comprises an active ingredient, such as an herbicide and an inactive ingredient such as a solvent or extender adjuvant. Encapsulation of a solid material can be accomplished by this method by forming a solution of the solid material in an appropriate solvent; thereby normally solid water-immiscible material can be encapsulated. For example, the insecticide N-(mercaptomethyl)phthalimide S-(O,O-dimethylphosphorodithioate), m.p. 72° C., can be encapsulated by first dissolving the solid in an appropriate solvent, such as heavy aromatic naphtha solvent.

What is claimed is:

1. In a process of encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps
    (a) providing at room temperature a dispersion of
        (i) a water-immiscible phase comprising the water-immiscible material to be encapsulated and organic polyisocyanates in
        (ii) an aqueous phase comprising a solution of water, a surfactant and a protective colloid; and
    (b) heating and maintaining said dispersion in a temperature range of about 40° C. to about 90° C., whereupon said water-immiscible material is encapsulated within discrete polyurea capsular enclosures directly usable without further separation or purification, the improvement comprising providing a plurality of water-immiscible phases each comprising at least one individually distinct wall-forming organic polyisocyanate monomer, and a water-immiscible material to be encapsulated in a polyurea wall formed from said polyisocyanate monomer, and sequentially or simultaneously dispersing each of said water-immiscible phases in said aqueous phase.

2. The process of claim 1 wherein the dispersed water-immiscible phase comprises droplets having a particle size of between about 0.5 microns to about 4000 microns.

3. The process of claim 2 wherein said dispersion is maintained by mild agitation.

4. The process of claim 3, wherein said water-immiscible phase contains a catalyst selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

5. The process of claim 3 wherein said dispersion includes a catalyst capable of increasing the rate of reaction of said organic polyisocyanates to form said polyurea.

6. The process of claim 5 wherein said catalyst is selected from the group consisting of a basic organic tertiary amine catalyst and an alkyl tin acetate catalyst.

7. The process of claim 1 wherein said dispersion includes a catalyst capable of increasing the rate of reaction of said organic polyisocyanates to form said polyurea.

8. The process of claim 7 wherein said catalyst is selected from the group consisting of a basic organic tertiary amine catalyst and an alkyl tin acetate catalyst.

9. The process of claim 1 wherein said water-immiscible phase contains a catalyst selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

10. Capsules capable of controlled release of encapsulated organic material comprising a thiocarbamate herbicide enclosed in a polyurea capsule produced by the process of claim 9.

11. Capsules capable of controlled release of encapsulated organic material comprising an organophosphorus insecticide enclosed in a polyurea capsule produced by the process of claim 9.

12. Capsules capable of controlled release of encapsulated organic material comprising an insect hormone mimic enclosed in a polyurea capsule produced by the process of claim 9.

* * * * *